United States Patent [19]

Hess

[11] Patent Number: 4,690,155
[45] Date of Patent: Sep. 1, 1987

[54] MONOPHASIC ACTION POTENTIAL RECORDING LEAD

[75] Inventor: Stanley R. Hess, Miami, Fla.

[73] Assignee: Cordis Corporation, Miami, Fla.

[21] Appl. No.: 945,242

[22] Filed: Dec. 24, 1986

Related U.S. Application Data

[63] Continuation of Ser. No. 752,141, Jul. 3, 1985, abandoned.

[51] Int. Cl.⁴ .............................................. A61N 1/04
[52] U.S. Cl. .................................. 128/786; 128/419 P
[58] Field of Search ............... 128/639, 642, 656, 657, 128/658, 419 P, 419 S, 772, 774, 783, 784, 786

[56] References Cited

U.S. PATENT DOCUMENTS

| | | | |
|---|---|---|---|
| 3,284,562 | 2/1965 | Stebleton | 128/419 P |
| 3,485,234 | 12/1969 | Stevens | 128/657 |
| 3,533,403 | 10/1970 | Woodson | 128/419 P |
| 3,664,347 | 5/1972 | Harmjanz | 128/419 P |
| 3,769,984 | 11/1973 | Muench | 128/786 |
| 3,911,928 | 10/1975 | Lagergren | 128/786 |
| 3,924,639 | 12/1975 | Hess | 128/786 |
| 3,977,411 | 8/1976 | Hughes, Jr. et al. | 128/786 |
| 4,124,028 | 11/1978 | Gallo | 128/419 S |

FOREIGN PATENT DOCUMENTS 2003138 1/1970 Fed. Rep. of Germany ...... 128/786

OTHER PUBLICATIONS

Article, "Long-Term Recording of Monophasic Action Potentials from Human Endocardium", Michael R. Franz, M.D., Reprinted from Jun. 1983 issue of The American Journal of Cardiology.

Primary Examiner—Edward M. Coven
Attorney, Agent, or Firm—Lockwood, Alex, Fitzgibbon & Cummings

[57] ABSTRACT

A monophasic action potential contact electrode catheter and method of producing same are provided. The catheter includes a compartmentalized tip portion that includes a distal tip electrode that was set in place within a distal tip compartment, as well as a lateral surface electrode that was set in place within a proximal compartment. The distal tip compartment and the proximal compartment are electrically insulated from each other, and the tip electrode has a surface at the distal end of the catheter that is suitable for contacting the tissue wall of locations at which monophasic action potential readings are to be taken.

5 Claims, 5 Drawing Figures

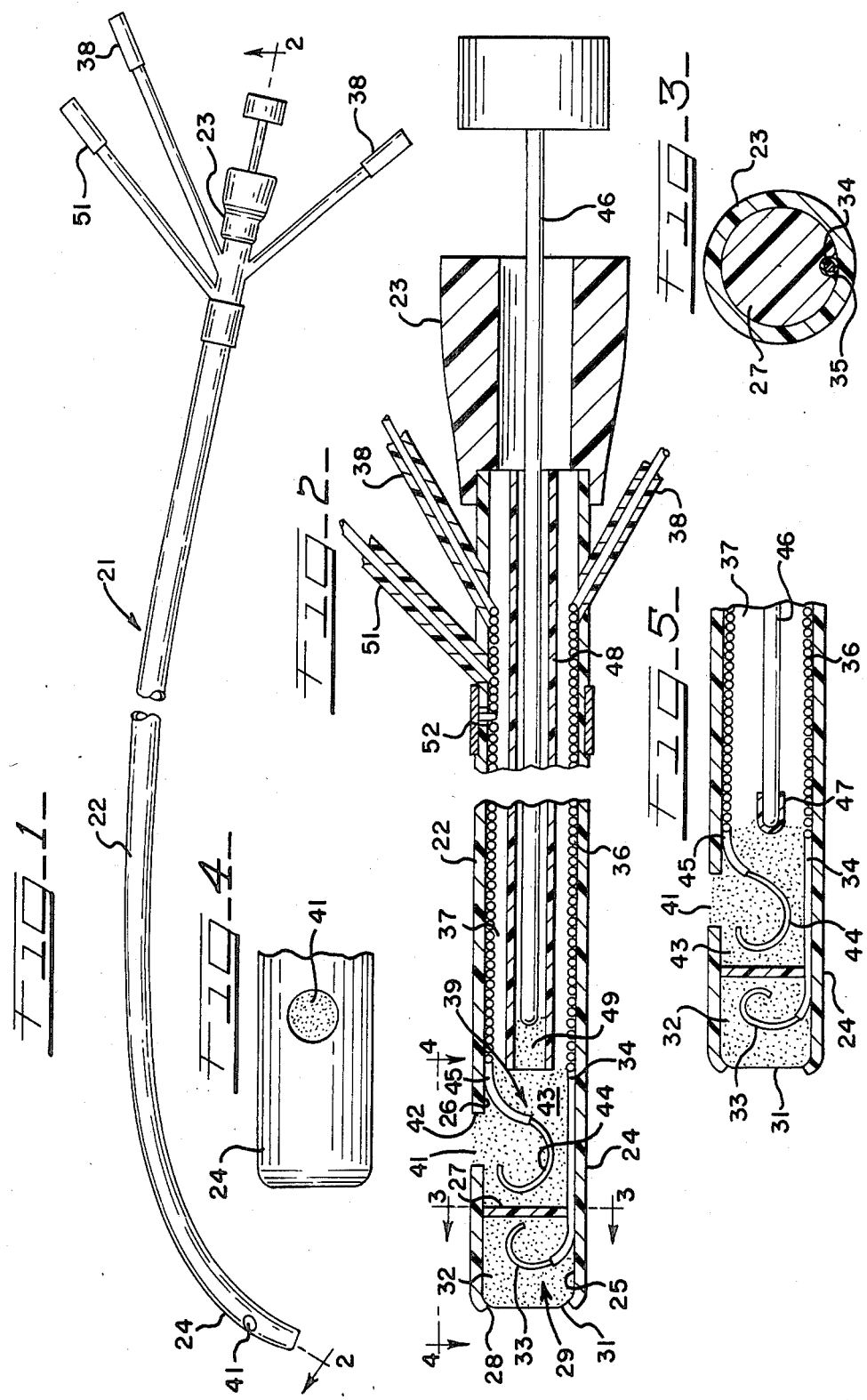

MONOPHASIC ACTION POTENTIAL RECORDING LEAD

This application is a continuation of application Ser. No. 752,141 filed July 3, 1985, abandoned.

BACKGROUND AND DESCRIPTION OF THE INVENTION

The present invention generally relates to a catheter for use in connection with the generation of monophasic action potential data for use in the study of the electrophysiology of cardiac tissue and the like. The catheter includes a contact electrode for touching the tissue to be subjected to the electrophysiological scrutiny, this contact electrode catheter including a compartmentalized tip portion. including a distal tip compartment and a proximal compartment. Each such compartment is in electrical communication with the proximal end of the catheter for electrical communication with a suitable recording device, and each compartment is filled with an electrically conductive filler material such as a thermoset resin or polymer that substantially fills each compartment in order to form a tip electrode and a lateral surface electrode. Access to the tip electrode is gained through an opening at the distal end of the catheter, while access to the lateral surface electrode is gained through an opening in the circumferential surface of the proximal compartment.

In conjunction with medical procedures such as cardiac catheterizations, it is often useful to study the electrophysiology of the tissue by obtaining and recording monophasic action potentials from endocardial sites. For example, bipolar recordings of monophasic action potentials are important in the study of drug-induced changes in the electrophysiology of the tissue. Monophasic action potential recordings are also useful for mapping the heart in order to find irritable foci. Such recordings can be used in evaluating changes in local myocardial electrical activity that are induced by pacing and/or that result from myocardial disease.

A previously developed approach for securing and recording monophasic action potentials include the application of suction electrodes to the cardiac tissue in an effort to accurately maintain the location of the electrode within a vigorously beating heart. Such suction electrodes transmit a monophasic signal that accurately reflects the onset of depolarization and the entire repolarization phase of transmembrane action potentials. Although the monophasic action potentials can be recorded accurately by the use of devices including suction electrodes, the use of suction in this context is designed to entrap cardiac tissue and can cause localized tissue damage. A response to this difficulty that has been developed includes the use of a contact electrode that eliminates the suction feature and that reports suitable monophasic action potentials by simply bringing the exploring electrode into firm approximation with the myocardial surface. Such contact electrode catheters permit easy and safe long-term monophasic action potential recording from the human endocardium during routine cardiac catheterization and the like. Monophasic action potential contact electrode catheters that have been developed in this regard utilize electrodes that are pellets of sintered silver-silver chloride.

The present invention improves upon previously known monophasic action potential contact electrode catheters and includes a compartmentalized tip portion of an elongated catheter body which preferably has torque-controlling properties in order to significantly assist in precisely locating the distal end of the catheter and in order to maintain that location for time periods, which may be extensive, during which it is desired to obtain and record monophasic action potentials. The compartmentalized tip portion includes a distal tip compartment housing a tip electrode and a proximal compartment housing a lateral surface electrode. Each of these electrodes includes a volume of conductor-loaded filler that had been injected and set and that is in electrical communication with the proximal end portion of the catheter.

It is accordingly a general object of this invention to provide an improved monophasic action potential contact electrode catheter.

Another object of the present invention is to provide a monophasic action potential catheter having a torque control body for assisting and maintaining the contact position of the catheter.

Another object of the present invention is to provide an improved monophasic action potential contact electrode catheter having an electrode structure that is relatively uncomplicated and efficient to manufacture and that is especially well suited for providing a structure that provides liquid tight sealing interfaces.

Another object of this invention is to provide an improved method for constructing a monophasic action potential contact electrode catheter.

Another object of the present invention is to provide a monophasic action potential contact electrode catheter and method of its construction which utilizes a thermosetting resin or polymer as the contact electrode.

Another object of this invention is to provide a monophasic action potential contact electrode catheter of the bipolar type in which the bipolar electrodes include filled and set thermoplastic which provides sealing surfaces that prevent blood from entering the catheter.

These and other objects, features and advantages of this invention will be clearly understood through a consideration of the following detailed description.

BRIEF DESCRIPTION OF THE DRAWINGS

In the course of this description, reference will be made to the attached drawings, wherein:

FIG. 1 is an elevational view, partially broken away, of the monophasic action potential contact electrode catheter according to this invention;

FIG. 2 is a substantially cross-sectional view of an embodiment of the contact electrode catheter illustrated in FIG. 1;

FIG. 3 is a cross-sectional view along the line 3—3 of FIG. 2;

FIG. 4 is a plan view taken along the line 4—4 of FIG. 2; and

FIG. 5 is a substantially cross-sectional view of a further embodiment of the monophasic action potential contact electrode catheter according to this invention.

DESCRIPTION OF THE PARTICULAR EMBODIMENTS

The monophasic action potential contact electrode catheter that is generally designated at 21 in FIG. 1 includes an elongated tubular body 22 having a hub assembly 23 at its proximal end portion, as well as a distal tip portion 24. The distal tip portion 24 is fused or otherwise secured to the elongated tubular body 22, or it may have a structure that is a substantially integral extension of one or more layers or components of the elongated tubular body 22. In any case, the distal tip portion 24 typically is more pliable and flexible and provides a more atraumatic external surface than does the elongated tubular body 22, which preferably exhibits torque-control properties.

Distal tip portion 24 has a compartmentalized structure that includes a distal tip compartment 25 and a proximal compartment 26. The distal tip compartment 25 and the proximal compartment 26 are each filled with a material that has electrically conductive properties and that was set therewithin. Distal tip compartment 25 and a proximal compartment 26 are electrically insulated from each other, for example by means of a non-conductive seperator disk 27. The outside diameter of the separator disk 27 is substantially the same as the inside diameter of the distal tip portion 24 in order to provide a snug fit therebetween and in order to provide a barrier between the material filled in the respective compartments 25 and 26.

Distal tip compartment 25 has an opening 28 at its distal end, which is also the distal end of the tip portion at 24 and of the catheter 21. A tip electrode, which is generally designated as 29, has a contact surface 31 which fills the opening 28. Tip electrode 29 and the distal tip compartment 25 are structured such that they provide a sealed interface which prevents blood and the like from entering the catheter 21.

In the preferred structure that is illustrated in the drawings, the tip electrode 29 includes a filled and set conductor-loaded resin or polymer plug 32 that had been thermoset in situ to embed therewithin a bared length 33 of otherwise insulated wire or conductor 34. The wire or conductor 34 exits the distal tip compartment 25 by passing, for example, through a notch 35 or a generally circular hole through the seperator disk 27. Insulated conductor 34 continues to pass through the catheter 21, preferably as part of a multifilar coil 36 that is positioned in lumen 37 of the elongated tubular body 22, the insulated conductor 34 exiting the catheter 21 for customary electrical connection with a terminal assembly 38.

A lateral surface electrode, generally designated as 39, is positioned within the proximal compartment 26 and has a lateral surface 41 that fills an opening 42 through the circumferential wall of the proximal compartment 26. Lateral surface electrode 39 includes a plug 43 of conductor-loaded set resin or polymer, together with a bared length 44 of an insulated conductor or wire 45 that is preferably a component of the multifilar coil 36. The insulated conductor 45 exits the catheter 21 and is in electrical communication with a suitable terminal assembly 38.

In the embodiment illustrated in FIG. 5, the lumen 37 accepts a stylet 46 to facilitate introduction of the monophasic action potential contact electrode catheter 21 into and through the body passage such as a vein or artery and to the desired location within the body. For example, stylet 46 serves to straighten the catheter 21 when it has a curved configuration such as that illustrated in FIG. 1, which is useful, for example, in facilitating introduction of the catheter 21 into the right ventricle of the heart. Stylet 46 includes an insulating cap 47 to prevent electrical communication between the stylet 46 and the plug 43 of conductor-loaded set resin or polymer. In the embodiment illustrated in FIG. 2, the stylet 46 slides through a sheath 48, which is sealed at its distal end with an insulating material 49.

The elongated tubular body 22 can have torque-control properties imparted thereto by having a multi-layered structure such as that described in U.S. Pat. No. 3,485,234. Such a multi-layered structure includes a tube of a polymer such as polyurethane or the like having a wire braid thereover, after which a material such as polyurethane is extruded over the wire braid. With this structure, the wire braid of the body provides an electromagnetic shield. A third terminal assembly 51 may be added to the proximal end of the catheter when such shielding is desired. Connection between the wire braid and the terminal assembly can be facilitated by wrapping a conductive band 52 over exposed wire braid.

Other body structures providing torque control could be substituted, particularly if the electromagnetic shield properties are not needed, as long as these torque-control structures have a diameter small enough and a wall size thin enough to suitably pass through a vein or the like.

Regarding the method of manufacturing the catheter 21, unless the external wall of the distal tip portion 24 is extruded together with the elongated tubular body 22, the distal tip portion wall and the distal end of the body 22 are fused together, and the distal tip is a hollow substantially cylindrical member that is coaxial with the elongated tubular body. The insulated conductors 34 and 45 are placed within the body, and the insulation along the distal end portion of each is removed in order form the bared lengths 33 and 44. The seperator disk 27 is placed between the bared lengths 33 and 44, and conductor-loaded resin or polymer is injected into each compartment that is thus formed thereby until the bared lengths 33 and 44 are both surrounded thereby and embedded therewithin. A preferred resin or polymer is a silver-loaded thermosetting material such as a silver-loaded epoxy resin.

The proximal compartment 26 is thus filled and set until lateral surface 41 is formed so as to be substantially isodiametric with the rest of the catheter 21. The distal tip compartment 25 is thus filled until the contact surface 31 is substantially flat as shown, although it may also be somewhat convex or somewhat concave, depending upon particular contact requirements. The thermoset resin or polyer of the electrodes 29 and 39 are then chlorodized by imersing the distal tip portion 24 into a hydrochloric acid bath and passing a current through the system in accordance with known procedures in order to form electrodes that do not have pure silver at their respective surfaces and that have enhanced electrical properties. Chlorodization procedures that are particularly suitable include those utilizing about ten milliamps of current for approximately four minutes. Because the thermoset material fills the opening 28 and the opening 42, a seal is provided which prevents blood from entering the lead.

In use, the monophasic action potential contact electrode catheter 21 is, typically with the aid of the stylet 46, inserted into the body. When monophasic action potential readings are to be taken in the right vetricle of the heart, the catheter is advanced, under fluoroscopic control, into the right ventricle. The stylet 46 may be removed completely or retracted from the distal portion of the catheter to permit reformation of the preformed curve, if provided. The catheter 21 is advanced until the contact surface 31 abuts a desired location on the endocardial surface of the right ventricle. With the terminal assemblies 38 connected to a suitable recording device (not shown) the monophasic action potentials are recorded for a desired length of time, and the catheter 21 is advanced to another site for proceeding with appropriate readings and recordings of monophasic action potentials at that site.

It will be understood that the embodiments of the present invention which have been described are illustrative of some of the applications of the principles of the present invention. Numerous modifications may be made by those skilled in the art without departing from the true spirit and scope of the invention.

I claim:

1. A monophasic action potential contact electrode catheter, comprising:

an elongated tubular body having a longitudinal lumen therethrough, said elongated tubular body having a proximal portion and a distal end, said proximal portion including a plurality of terminal assemblies;

a compartmentalized tip portion extending from said distal end of the tubular body, said compartmentalized tip portion including a generally cylindrical wall member;

said compartmentalized tip portion includes a distal tip compartment having a circumferential surface and a proximal compartment having a circumferential surface, said distal tip compartment circumferential surface and said proximal compartment circumferential surface being substantially coextensive and defined by said generally cylindrical wall member, said distal tip compartment and said proximal compartment being electrically insulated from each other, said distal tip compartment having an opening at its distal end, and said proximal compartment having an opening in its said circumferential surface;

a tip electrode within said distal tip compartment and including an uninsulated length of a first electrically conductive wire in electrical communication with one of said terminal assemblies of the proximal portion of the tubular body, said tip electrode including a conductor-loaded material that is an injected and set resin or polymer plug that substantially fills said distal tip compartment and that is exposed through said distal end opening of the distal tip compartment, said uninsulated length of the first electrically conductive wire being encapsulated by and embedded within said tip electrode conductor-loaded material;

a lateral surface electrode within said proximal compartment and including an uninsulated length of a second electrically conductive wire in electrical communication with another of said terminal assemblies of the proximal portion of the tubular body, said lateral surface electrode including a conductor-loaded material that is an injected and set resin or polymer plug that substantially fills said proximal compartment and that is exposed through said circumferential surface opening of the proximal compartment, said uninsulated length of the second electrically conductive wire being encapsulated by and embedded within said lateral surface electrode conductor-loaded material;

each of said plugs is a thermoset and chlorodized resin or polymer that is filled with conductive particles substantially throughout the respective volumes of the plugs, said plug of the tip electrode defines a sealed interface of the tip electrode along said distal end opening, and said plug of the proximal electrode defines a sealed interface of the lateral surface electrode along said circumferential surface opening; and a non-conductive separator member within said compartmentalized tip portion, said non-conductive separator member defining said distal tip compartment and said proximal compartment and electrically insulating said distal tip compartment from said proximal compartment, said non-conductive separator member being substantially disk-shaped and being transversely positioned within said generally cylindrical wall member.

2. The monophasic action potential contact electrode catheter according to claim 1, wherein said thermosetting material is an epoxy resin, and said loaded conductor is silver.

3. The monophasic action potential contact electrode catheter according to claim 1, wherein said elongated tubular body has torque-control properties, and said generally cylindrical wall member of the compartmentalized tip portion is substantially flexible.

4. The monophasic action potential contact electrode catheter according to claim 1, wherein said substantially disk-shaped separator member which electrically insulates said distal tip compartment from said proximal compartment has a peripheral size that is substantially the same as that of the generally cylindrical wall member of the compartmentalized tip portion so as to provide a snug fit between said separator member and said generally cylindrical wall member, and wherein said separator member includes an orifice therethrough for snugly receiving an insulated portion of said first electrically conductive wire.

5. The monophasic action potential contact electrode catheter according to claim 1, wherein said elongated tubular body member includes a wire braiding electromagnetic shield, said wire braiding being in electrical communication with a further one of said proximal portion terminal assemblies.

* * * * *

UNITED STATES PATENT AND TRADEMARK OFFICE
CERTIFICATE OF CORRECTION

PATENT NO. : 4,690,155
DATED : September 1, 1987
INVENTOR(S) : Stanley R. Hess

It is certified that error appears in the above—identified patent and that said Letters Patent is hereby corrected as shown below:

In the ABSTRACT, line 11, "of" should read --at--.
Column 2, line 68, "integal" should read --integral--.
Column 3, lines 15 and 36, "seperator" should read --separator--.
Column 4, line 30, "seperator" should read --separator--; line 46, "imersing" should read --immersing--; line 60, "vetricle" should read --ventricle--; line 66, "abutts" should read --abuts--.

Signed and Sealed this

Twenty-seventh Day of September, 1988

Attest:

DONALD J. QUIGG

Attesting Officer

Commissioner of Patents and Trademarks